(12) United States Patent
Takahashi

(10) Patent No.: US 9,884,045 B2
(45) Date of Patent: Feb. 6, 2018

(54) TRANSPLANTATION ADJUVANT IN CELL THERAPY USING NEURAL PROGENITOR CELLS

(71) Applicant: Sumitomo Dainippon Pharma Co., Ltd., Osaka (JP)

(72) Inventor: Jun Takahashi, Kyoto (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 14/891,601

(22) PCT Filed: Nov. 14, 2013

(86) PCT No.: PCT/JP2013/080816
§ 371 (c)(1),
(2) Date: Nov. 16, 2015

(87) PCT Pub. No.: WO2014/184973
PCT Pub. Date: Nov. 20, 2014

(65) Prior Publication Data
US 2016/0106719 A1 Apr. 21, 2016

(30) Foreign Application Priority Data
May 16, 2013 (JP) .................. 2013-104329

(51) Int. Cl.
*A61K 31/423* (2006.01)
*A61K 31/19* (2006.01)
*A61K 31/20* (2006.01)

(52) U.S. Cl.
CPC ............ *A61K 31/423* (2013.01); *A61K 31/19* (2013.01); *A61K 31/20* (2013.01)

(58) Field of Classification Search
CPC ...... A61K 31/423; A61K 31/19; A61K 31/20; A61K 2300/00
See application file for complete search history.

(56) References Cited

U.S. PATENT DOCUMENTS

2007/0078083 A1* 4/2007 Barlow .................. A61K 31/16
514/8.3

FOREIGN PATENT DOCUMENTS

JP 2009-050172 A 3/2009

OTHER PUBLICATIONS

Hsieh et al., "Histone deacetylase inhibition-mediated neuronal differentiation of mulitpotent adult neural progenitor cells," PNAS, 101: 16659-16664 (2004).
Abematsu et al., "Neurons derived from transplanted neural stem cells restore disrupted neuronal circuitry in a mouse model of spinal cord injury," Journal of Clinical Investigation, 120: 3255-3266 (2010).
Yoshikawa et al., "Systemic administration of valproic acid and zonisamide promotes differentiation of induced pluripotent stem cell-derived dopaminergic neurons," Frontiers in Cellular Neuroscience, 7: 11 (2013).
Murata, "The discovery of an antiparkinsonian drug, zonisamide," Clinical Neurology, 50: 780-782 (2010) (see English abstract).
Kidd et al., "Protective Effects of Valproic Acid on the Nigrostriatal Dopamine System in a 1-Methyl-4-Phenyl-1,2,3,6-Tetrahydropyridine Mouse Model of Parkinson's Disease," Neuroscience, 194: 189-194 (2011).
Svendsen et al., "Long-Term Survival of Human Central Nervous System Progenitor Cells Transplanted into a Rat Model of Parkinson's Disease," Experimental Neurology, 148: 135-146 (1997).
Yokoyama et al., "Therapeutic effect of zonisamide on the nigrostriatal dopaminergic neurons in the 1-methyl-4-phenyl-1,2,3,6-tetrahydropyridine (MPTP)-induced mice model of Parkinson's disease," Journal of Pharmacological Sciences, 118: 115P (2012).
Chen et al., "Valproate protects dopaminergic neurons in midbrain neuron/glia cultures by stimulating the release of neurotrophic factors from astrocytes," Molecular Psychiatry, 11: 1116-1125 (2006).
Samata et al., "Maturity and protective action of midbrain dopaminergic neuronal cell resulting from administering valproic acid," Japanese Society for Regenerative Medicine Sokai Program Shoroku, 301 (2013).
International Preliminary Report on Patentability and Written Opinion issued in corresponding International Patent Application No. PCT/JP2013/080816 dated Nov. 26, 2015.
International Search Report issued in corresponding International Patent Application No. PCT/JP2013/080816 dated Feb. 10, 2014.

* cited by examiner

*Primary Examiner* — Sarah Pihonak
*Assistant Examiner* — Jason Deck
(74) *Attorney, Agent, or Firm* — Morgan, Lewis & Bockius LLP

(57) ABSTRACT

The present invention provides a transplantation adjuvant for neural progenitor cells containing valproic acid and/or zonisamide as an active ingredient.

19 Claims, 8 Drawing Sheets

(A)

(B)

(A)

(B)

(A)

(B)

TRANSPLANTATION ADJUVANT IN CELL THERAPY USING NEURAL PROGENITOR CELLS

TECHNICAL FIELD

The present invention relates to a transplantation adjuvant in cell therapy using neural progenitor cells.

BACKGROUND ART

Parkinson's disease is a progressive neurodegenerative disease, and is characterized by loss of nigrostriatal dopaminergic nerves (dopaminergic neurons). It has been confirmed through clinical studies made until now that a motor symptom of a Parkinson's disease patient is improved by transplantation of fetal midbrain cells. Based on this fact, cell replacement therapy is presumed to be employed as a treatment method for Parkinson's disease.

CITATION LIST

Non Patent Literature

Non Patent Literature 1: Hsieh, J. et al., Proc. Natl. Acad. Sci. USA (2004) 101, 16659-16664
Non Patent Literature 2: Abematsu, M. et al., J Clin. Invest., (2010) 120, 3255-3266

SUMMARY OF INVENTION

Problems to be Solved by the Invention

Pluripotent stem cells, particularly induced pluripotent stem cells (iPS cells), have a possibility of supplying a large amount of dopaminergic neurons. Therefore, pluripotent stem cells are regarded as a novel donor cell source. According to the findings obtained by the present inventors, however, neural progenitor cells and dopaminergic neurons differentiated from stem cells like iPS cells have an extremely low retention rate (hereinafter sometimes referred to as "survival rate") after transplantation into a brain.

Accordingly, an object of the present invention is to provide a transplantation adjuvant for neural progenitor cells with which a retention rate of dopaminergic neurons induced from transplanted neural progenitor cells can be improved.

Means for Solving the Problems

The present inventors found that a retention rate of dopaminergic neurons after transplantation is improved by administering, to a subject, valproic acid or zonisamide, used as an antiepileptic drug, as adjuvant in transplantation of neural progenitor cells, resulting in accomplishing the present invention.

It has been conventionally reported that valproic acid differentiates hippocampal neural progenitor cells into neurons in an in vitro system (Non Patent Literature 1), and that differentiation into neurons is accelerated in a model mouse suffering from spinal injury by administering valproic acid at the same time as transplantation of neural stem cells (Non Patent Literature 2). It has not been known, however, that valproic acid improves a retention rate of differentiation induced dopaminergic neurons after transplantation. Also with respect to zonisamide, that is, an antiepileptic drug, there have been no findings about improvement of a retention rate of neural progenitor cells and dopaminergic neurons after transplantation.

Specifically, the present invention pertains to the following:

[1] A transplantation adjuvant for neural progenitor cells comprising valproic acid and/or zonisamide as an active ingredient.

[2] The transplantation adjuvant according to [1] described above, to be administered no sooner than two days before transplanting the neural progenitor cells.

[3] The transplantation adjuvant according to [1] or [2] described above, in which the neural progenitor cells are derived from iPS cells.

[4] The transplantation adjuvant according to any one of [1] to [3] described above, used for treating a degenerative disease of dopaminergic neurons.

[5] The transplantation adjuvant according to [4] described above, in which the degenerative disease of dopaminergic neurons is Parkinson's disease.

[6] The transplantation adjuvant according to any one of [1] to [5] described above, used for administering, to a human, 100 to 1200 mg per day of the valproic acid or 10 to 600 mg per day of the zonisamide.

[7] The transplantation adjuvant according to any one of [1] to [6] described above, to be administered, to a human, no sooner than two days before transplanting the neural progenitor cells.

The present invention further pertains to the following:

[8] A method for improving a retention rate of dopaminergic neurons induced from neural progenitor cells after transplantation, including administering an effective amount of valproic acid and/or zonisamide to a mammal into which the neural progenitor cells have been transplanted.

[9] The method according to [8] described above, in which the mammal is a human.

[10] The method according to [8] or [9] described above, in which the effective amount of valproic acid and/or zonisamide is administered no sooner than two days before transplanting the neural progenitor cells.

[11] The method according to any one of [8] to [10] described above, in which the neural progenitor cells are derived from iPS cells.

[12] The method according to any one of [8] to [11] described above, in which the mammal has a degenerative disease of dopaminergic neurons.

[13] The method according to [12] described above, in which the degenerative disease of dopaminergic neurons is Parkinson's disease.

[14] The method according to any one of [8] to [13] described above, in which the effective amount is 100 to 1200 mg per day of the valproic acid or 10 to 600 mg per day of the zonisamide.

[15] The method according to any one of [8] to [14] described above, in which the effective amount of valproic acid and/or zonisamide is administered to a human no sooner than two days before transplanting the neural progenitor cells.

[16] Valproic acid and/or zonisamide for use in improving a retention rate of dopaminergic neurons induced from neural progenitor cells transplanted into a mammal.

[17] The valproic acid and/or zonisamide according to [16] described above, to be administered no sooner than two days before transplanting the neural progenitor cells.

[18] The valproic acid and/or zonisamide according to [16] or [17] described above, in which the neural progenitor cells are derived from iPS cells.

[19] The valproic acid and/or zonisamide according to any one of [16] to [18] described above, in which the mammal has a degenerative disease of dopaminergic neurons.

[20] The valproic acid and/or zonisamide according to [19] described above, in which the degenerative disease of dopaminergic neurons is Parkinson's disease.

[21] The valproic acid and/or zonisamide according to any one of [16] to [20] described above, used to be administered, to a human, 100 to 1200 mg per day of the valproic acid or 10 to 600 mg per day of the zonisamide.

[22] The valproic acid and/or zonisamide according to any one of [16] to [21] described above, to be administered, to a human, no sooner than two days before transplanting the neural progenitor cells.

Effects of the Invention

According to the present invention, a transplantation adjuvant for neural progenitor cells with which a retention rate of dopaminergic neurons induced from transplanted neural progenitor cells can be improved can be provided.

EMBODIMENTS FOR CARRYING OUT THE INVENTION

Figure 1:
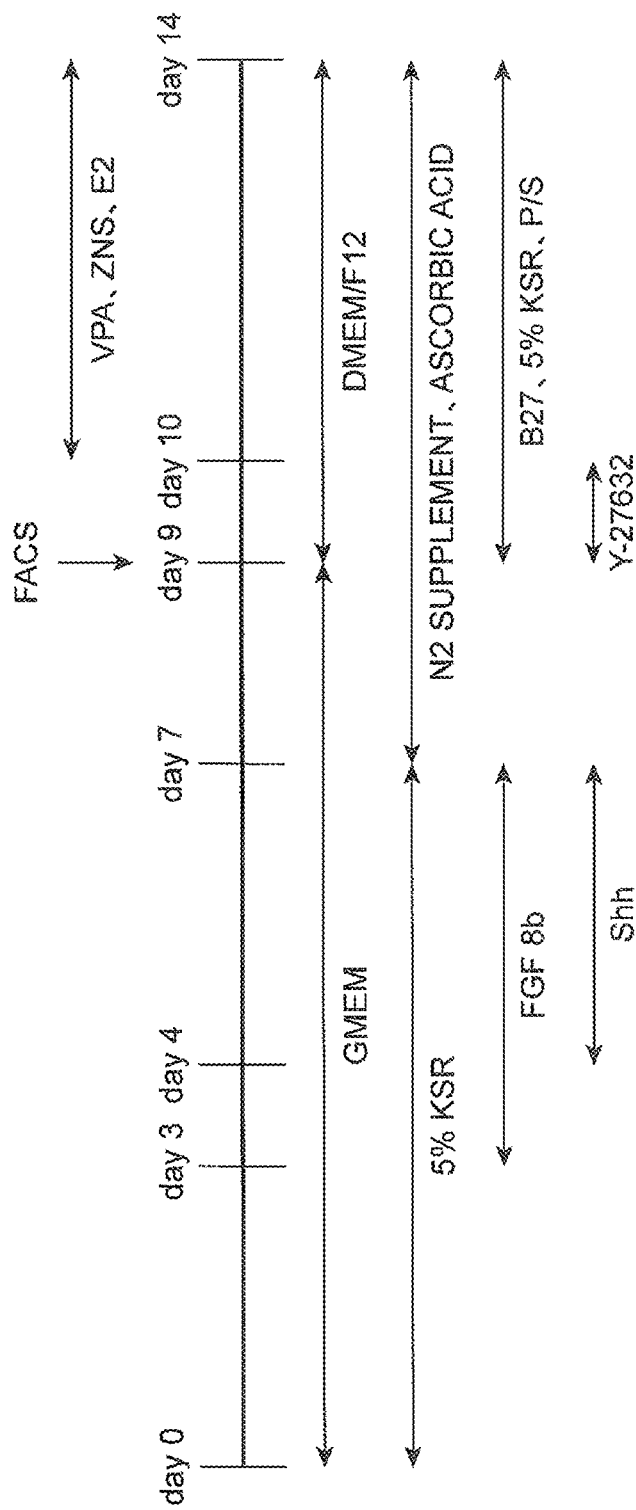
FIG. 1 is a diagram illustrating a schedule for differentiation induction of mouse iPS cells through neural progenitor cells into midbrain dopaminergic neurons.

Preferred embodiments of the present invention will now be described in detail. It is noted, however, that the present invention is not limited to the following embodiments.

A transplantation adjuvant for neural progenitor cells (hereinafter sometimes simply referred to as the "transplantation adjuvant") of the present embodiment contains, as an active ingredient, valproic acid (chemical name: sodium 2-propylpentanoate) and/or zonisamide (chemical name: 1,2-benzisoxazole-3-methanesulfonamide) (hereinafter, valproic acid and zonisamide are sometimes designated respectively as "VPA" and "ZNS").

Here, a transplantation adjuvant means an agent for assisting transplantation for attaining a desired effect of cell transplantation by improving a retention rate of transplanted cells, by leading transplanted cells into a desired cell type, by preventing tumorigenesis of transplanted cells, or the like. A transplantation adjuvant can be grasped as, for example, an agent for improving survival rate, an agent for improving a graft survival rate or an agent for improving a differentiation induction for neurons of interest after transplantation. It can be determined whether or not a retention rate of phenotypic neurons of interest (midbrain dopaminergic neurons) after transplantation has been improved depending on, for example, whether or not dopamine producing cells remaining seven days to four weeks after the transplantation or an increase rate of production or the like of brain dopamine is statistically significant as compared with that of a control, or whether or not the size of a graft is unchanged with time. Here, since there is no problem even if a duration from the transplantation to a test for making the aforementioned determination is longer, the duration from the transplantation to the test is not limited to "seven days to four weeks", but the upper limit is not specified.

The transplantation adjuvant may contain, as an active ingredient, valproic acid or zonisamide singly, or both valproic acid and zonisamide. For example, valproic acid is available from Sigma-Aldrich, and zonisamide is available from Sumitomo Dainippon Pharma Co., Ltd.

The transplantation adjuvant may contain merely the active ingredient of valproic acid and/or zonisamide alone, or may contain both the active ingredient and another component. Examples of another component include a pharmaceutically acceptable carrier, a filler, a binder, a stabilizer, a buffer, a solubilizer, and an isotonic agent. In addition, suitable another component can be appropriately prepared in accordance with oral or parenteral administration.

To "contain as an active ingredient" includes not only a case where valproic acid or zonisamide is in a free form of an acid or the like but also a case where the transplantation adjuvant contains such a component in the form of a pharmaceutically acceptable salt. An example of the pharmaceutically acceptable salt includes sodium salt.

Although it is varied depending on various conditions including the symptom, the age and the weight of a patient, in a case of oral administration to a human, the transplantation adjuvant can contain, as the active ingredient, 100 to 1200 mg or 400 to 1200 mg of valproic acid per daily dose. In the case of oral administration to a human, the transplantation adjuvant can contain, as the active ingredient, 10 to 600 mg or 25 to 200 mg of zonisamide per daily dose.

The neural progenitor cells to which the transplantation adjuvant is applied mean cells capable of differentiating into neurons.

The neural progenitor cells may be cells isolated from a brain tissue of a mammal such as a human. The neural progenitor cells may be cells obtained through differentiation induction from pluripotent stem cells such as embryonic stem cells (ES cells) and iPS cells (which are respectively sometimes designated as ES cell-derived cells and iPS-cell derived cells). An example of the cells isolated from a brain tissue includes cells contained in a midbrain tissue of an embryo described in, for example, Nature Neuroscience, 2, 1137 (1999) or N. Engl. J. Med.; 334: 710-9 (2001). The neural progenitor cells may be dopamine-producing progenitor cells.

If the neural progenitor cells are isolated from a brain tissue of a mammal such as a human, they can be isolated by a known method such as flow cytometry by using, as an index, a marker molecule specifically expressed in the neural progenitor cells or neurons, such as PSA-NCAM, CD24 or Corin.

If the neural progenitor cells are obtained through the differentiation induction from stem cells such as ES cells or iPS cells, any of known methods can be employed. Examples of a method for differentiating the neural progenitor cells from iPS cells include: (1) serum-free floating culture of embryoid bodies-like aggregates (SFEB) (Watanabe K. et al., Nat. Neurosci. 8: 288-96, 2005), (2) a method for differentiating pluripotent stem cells through culture on stromal cells (SDIA method) (Kawasaki H. et al., Neuron. 28: 31-40, 2000), (3) a method for culturing with an agent added to Matrigel (Chambers S M. et al., Nat. Biotechnol. 27: 275-80, 2009), and (4) a method using a low molecular weight compound (Morizane A. et al., J. Neurosci. Res. 89: 117-126, 2011). As a method for isolating neural progenitor cells differentiated from pluripotent stem cells, a method similar to one employed for isolating the neural progenitor cells from a brain tissue of a mammal such as a human may be employed.

Here, a pluripotent stem cell means a stem cell that has pluripotency capable of differentiating into any of all cells present in an organism, and in addition, has proliferation potency. Examples of the pluripotent stem cell include, but are not especially limited to, an embryonic stem (ES) cell, a cloned embryo-derived embryonic stem (ntES) cell obtained by nuclear transplantation, a spermatogonial stem cell (GS cell), an embryonic germ cell (EG cell), an induced pluripotent stem (iPS) cell, and a cultured fibroblast- or a bone marrow stem cell-derived pluripotent stem cell (Muse cell). The pluripotent stem cell may be an ES cell, an ntES cell or an iPS cell. In consideration of an ethical point, the pluripotent stem cell may be an iPS cell.

An ES cell can be produced from a fertilized egg derived from a mammal. Examples of the mammal include a mouse, a rat, a guinea pig, a hamster, a rabbit, a cat, a dog, a sheep, a pig, a bovine, a horse, a goat, a monkey and a human. The mammal may be a human.

Specifically, a blastocyst developed from a fertilized egg is cultured together with feeder cells to increase an inner cell mass. Thereafter, an operation to isolate cells derived from the increased inner cell mass into single cells and to subculture the resultant cells with the feeder cells is repeated, and thus, an ES cell line can be obtained (Thomson J A. et al. (1998), Science. 282: 1145-1147 and H. Suemori et al. (2006), Biochem. Biophys. Res. Commun., 345: 926-932).

An iPS cell can be produced from a somatic cell derived from a mammal. Examples of the mammal include a mouse, a rat, a guinea pig, a hamster, a rabbit, a cat, a dog, a sheep, a pig, a bovine, a horse, a goat, a monkey and a human. The mammal may be a human.

A specific example includes a cell that is obtained by introducing a plurality of prescribed reprogramming factors into a somatic cell such as a skin cell and has acquired multipotency. Examples of the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3 and Glis1. One of these reprogramming factors may be singly used or, a combination of these may be used. Examples of the combination of the reprogramming factors include those described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D., et al. (2008), Nat. Biotechnol., 26: 795-797, Shi Y., et al. (2008), Cell Stem Cell, 2: 525-528, Eminli S., et al. (2008), Stem Cells. 26:2467-2474, Huangfu D., et al. (2008), Nat. Biotechnol. 26:1269-1275, Shi Y., et al. (2008), Cell Stem Cell, 3, 568-574, Zhao Y., et al. (2008), Cell Stem Cell, 3:475-479, Marson A., (2008), Cell Stem Cell, 3, 132-135, Feng B., et al. (2009), Nat. Cell Biol. 11:197-203, R. L. Judson et al., (2009), Nat. Biotech., 27:459-461, Lyssiotis C A., et al. (2009), Proc. Natl. Acad. Sci. USA. 106:8912-8917, Kim J B., et al. (2009), Nature. 461:649-643, Ichida J K., et al. (2009), Cell Stem Cell. 5:491-503, Heng J C., et al. (2010), Cell Stem Cell. 6:167-74, Han J., et al. (2010), Nature. 463:1096-100, Mali P., et al. (2010), Stem Cells. 28:713-720, Maekawa M., et al. (2011), Nature. 474:225-9. The combination of the reprogramming factors may be a combination of Oct3/4, Klf4 and Sox2.

Besides, iPS cells are available from specific institutions (such as Kyoto University). For example, a 440A3 cell line, that is, a mouse-derived iPS cell line obtained by introducing Oct3/4 gene, Klf4 gene and Sox2 gene, is available from Kyoto University. Examples of a human-derived iPS cell line include 201B7, 409B2 and 1039A1.

Also when the neural progenitor cells are ES cell-derived cells, similar effects can be attained.

The transplantation adjuvant can be used to be administered to a mammal of interest before or after transplanting the neural progenitor cells into the mammal or at the same time as the transplantation. The transplantation adjuvant may be used to be administered no sooner than two days before transplanting the neural progenitor cells. If the transplantation adjuvant is administered no sooner than two days before transplanting the neural progenitor cells, the transplantation can be conducted in a state where the active ingredient retains an effective blood concentration. Here, "two days before transplanting the neural progenitor cells" means two days before a day when the neural progenitor cells are transplanted into the mammal of interest.

Examples of the mammal of interest include a mouse, a rat, a guinea pig, a hamster, a rabbit, a cat, a dog, a sheep, a pig, a bovine, a horse, a goat, a monkey and a human. The transplantation adjuvant of the present embodiment may be used in a human.

Although it is varied depending on the purpose of administration, the method of administration and the situation of an administration subject (such as the sex, the age, the weight and the condition of a disease), in a case of administration to a human, for example, the transplantation adjuvant may be used so that 100 to 1200 mg or 400 to 1200 mg of the valproic acid can be administered per day. For example, the transplantation adjuvant may be used so that 10 to 600 mg or 25 to 200 mg of the zonisamide can be administered per day.

If the transplantation adjuvant is administered at the above-described dose once a day, it may be used to be administered to the mammal of interest at least once or more. If the transplantation adjuvant is administered at the above-described dose once a day, it may be used to be administered to the mammal of interest 60 through 180 times or 90 through 120 times.

The route of the administration of the transplantation adjuvant may be either oral administration or parenteral administration, and may be oral administration. Examples of usually employed dosage form include tablets, capsules, granules, fine granules, powders, sublingual tablets, syrups and suspensions. The transplantation adjuvant in a liquid form may be parenterally administered as an injection. The above-described dosage forms can be produced by mixing valproic acid and/or zonisamide as the active ingredient with acceptable usual carrier, filler, binder, stabilizer and the like. If the transplantation adjuvant is used as an injection, an acceptable buffer, solubilizer, isotonic agent and the like may be added thereto.

When the transplantation adjuvant is administered to the mammal of interest, retention ratios of the neural progenitor cells and dopaminergic neurons differentiated from the neural progenitor cells after the transplantation are improved. Therefore, the transplantation adjuvant may be also used for treating or preventing a degenerative disease of dopaminergic neurons.

A degenerative disease of dopaminergic neurons refers to a disease caused when the dopaminergic neurons are reduced, and the examples include Parkinson's disease and dementia with Lewy body.

The present invention has been specifically described with reference to the embodiment so far, but the present invention is not limited to the above-described embodiment. For example, the transplantation adjuvant of the present invention may be added to neural progenitor cells in vitro to prepare cells for transplantation of dopaminergic neurons or the like, and thereafter, the thus obtained cells for transplantation may be transplanted into a brain region or the like. In this case, the transplantation adjuvant is added in an amount sufficient for differentiation into desired cells for transplantation, and after retaining it for, for example, 48 to 192 hours, the resultant cells are transplanted into a target brain region. After transplanting the cells for transplantation into the target brain region, the transplantation adjuvant of the present invention may be further systemically administered to the transplanted mammal.

EXAMPLES

Materials and Methods

Differentiation of Dopaminergic Neurons from Mouse iPS cells

The 440A3 cells, that is, a mouse iPS cell line, were used after 10 to 25 passages. The 440A3 cells produced by using a plasmid vector having three genes of Oct3/4, Klf4 and Sox2 had a green fluorescent protein (GFP) and a puromycin resistance gene under control of Nanog enhancer and promotor. The GFP gene and the puromycin resistance gene are activated merely when the 440A3 cells are not differentiated. There is no report on integration of an exogenous gene in the 440A3 cells.

The undifferentiated 440A3 cells were maintained in a DMEM (Dulbecco's Modified Eagle Medium, manufactured by Wako Pure Chemical Industries, Ltd.) together with mouse embryo fibroblasts (MEF) (feeder cells) having been treated with mitomycin C. In this manner, unintentionally differentiated 440A3 cells were removed. The DMEM contained 1% fetal bovine serum (FBS), 5% knockout serum replacement (KSR; manufactured by Invitrogen), 0.1 mM non-essential amino acids, 1 mM sodium pyruvate, 0.1 mM 2-mercaptoethanol (2-ME; manufactured by Invitrogen), 2000 U/ml leukemia inhibitory factor (manufactured by Invitrogen), and 1.5 µg/ml puromycin. In order to differentiate and induce the iPS cells into neural cells, serum-free floating culture of embryoid bodies-like aggregates (SFEB) was employed. Specifically, aggregates of the 440A3 cells were separated into individual cells by using 0.25% trypsin/1 mM EDTA (ethylenediaminetetraacetic acid), and the resultant cells were seeded in a 96-well low adhesion plate (product name: Lipidure-Coat Plate A-US96, manufactured by NOF Corporation) at a concentration (cell density) of 3000 cells/well. Thereafter, re-aggregation of the 440A3 cells was induced in a differentiation medium containing GMEM (Glasgow Minimum Essential Medium), 5% KSR, 0.1 mM non-essential amino acids, 1 mM sodium pyruvate and 0.1 mM 2-ME, and this day was defined as day 0 (FIG. 1). During this differentiation process, various factors were added to the differentiation medium for inducing midbrain dopaminergic phenotypes as illustrated in FIG. 1. Specifically, from day 3 to day 7 after starting the SFEB, 20 ng/ml of mouse FGF-8b (manufactured by R & D Systems) was added, from day 4 to day 7 after starting the SFEB, 10 ng/ml of recombinant mouse sonic hedgehog (C25II) N-terminus (manufactured by R & D Systems) was added, and on and after day 7 after starting the SFEB, 1% N-2 supplement (manufactured by Gibco) and 200 nM ascorbic acid were added. The KSR was removed from the differentiation medium on day 7 after starting the SFEB.

Fluorescence-Activated Cell Sorting (FACS)

On day 9 after starting the SFEB, the 440A3 cells were washed with phosphate buffered saline (PBS(-)) twice. Thereafter, the 440A3 cells were dissociated into single cells by five-minute incubation performed at 37° C. by using Accumax (manufactured by Innovate Cell Technologies, product name). The cells were collected with a FACS buffer. The FACS buffer was constituted by PBS(-) containing 2% FBS, 20 mM D-glucose and 1% penicillin/streptomycin (P/S, manufactured by Invitrogen). The collected cells were mechanically dissociated into a single cell suspension by a gentle pipetting operation.

Next, the resultant cells were incubated with a mouse anti-PSA-NCAM antibody (dilution rate of 1:200, manufactured by Millipore) at 4° C. for about 30 minutes. Thereafter, a washing operation using a centrifuge was performed twice, and the resultant cells were further incubated for 30 minutes with a secondary antibody of a donkey anti-mouse IgG (dilution rate of 1:400, manufactured by Invitrogen) labeled with AlexaFluor 594. Dead cells and cell debris were excluded by using 7-aminoactinomycin-D (7-AAD, manufactured by BD Pharmigen) stain. The remaining living cells were suspended again at a final concentration (cell density) of $1 \times 10^7$ cells/ml. Cell sorting was conducted by using a FACSAria II cell sorter (manufactured by Becton Dickinson And Company) equipped with a 488 nm argon laser, a 633 nm helium-neon laser, a 100 µm nozzle and a FACSDiva software program. A PSA-NCAM positive rate was determined on the basis of a negative control not using a primary antibody.

In vitro Treatment for Differentiation Inducing Neural Progenitor Cells into Dopaminergic Neurons by using Test Compound After the cell sorting, in order to induce the reaggregation of the cells, a PSA-NCAM$^+$ cell group was seeded in a DMEM/F12 medium (manufactured by Wako Pure Chemical Industries, Ltd.) in a 96-well plate at a concentration (cell density) of 20000 cells/well. The DMEM/F12 medium contained 1% N-2 supplement, 200 nM ascorbic acid, 2% B27 supplement (manufactured by Invitrogen), 0.5 mM L-glutamine and 1% P/S. In order to prevent apoptosis, a ROCK inhibitor, Y-27632 (manufactured by Wako Pure Chemical Industries, Ltd.), was used at a concentration of 30 µM during the cell sorting process and the following overnight cultivation. On day 10 after starting the SFEB, any one of valproic acid (VPA) (manufactured by Sigma-Aldrich), zonisamide (ZNS) sodium salt (manufactured by Sumitomo Dainippon Pharma Co., Ltd.), 17β estradiol (E2) (manufactured by Sigma-Aldrich), a glial cell line derived neurotrophic factor (GDNF) (manufactured by R & D Systems) and PBS(-) was added to the medium for 4 days. Each of VPA, ZNS and E2 was used at three different concentrations. Specifically, the concentration of VPA was 0.01 mM, 0.1 mM or 1 mM, the concentration of ZNS was 1 µM, 10 µM or 100 µM, and the concentration of E2 was 1 nM, 10 nM or 100 nM. GDNF was added at a concentration of 20 mg/ml to be used as a positive control. In order to neutralize the effect of VPA and E2, 2,5-dideoxyadenosine (ddA, 100 µM; manufactured by Santa Cruz Biotechnology, Inc.), that is, an adenylate cyclase inhibitor, and ICI182780 (ICI, 2 µM; manufactured by Wako Pure Chemical Industries, Ltd.), that is, an estrogen receptor antagonist, were respectively added to the media on day 10 after starting the SFEB.

Transplantation Experiment of Mouse iPS Cell-derived Dopamine Neural Progenitor Cells Ten-week-old Sprague-Dawley rats (SD rats, available from Shimizu Laboratory Supplies Co., Ltd.) were handled in accordance with the Guidelines for Animal Experiments of Kyoto University. Each SD rat was anesthetized, and donor cells were transplanted by stereotaxic injection into striatums on both sides. Two cell aggregates (containing $3.1 \times 10^5$ cells on average) obtained on day 9 after starting the SFEB were collected in 1 µl of PBS(-) so as to be used as the donor cells for the transplantation in each tract. To the PBS(-), Y-27632 was added at a final concentration of 30 µM. Thereafter, intraperitoneal injection of VPA (150 mg/kg/day), ZNS sodium salt (30 mg/kg/day), E2 (80 µM/kg/day) or a saline was conducted from two days before transplanting the donor cells until a day of necropsy. For immunosuppression, cyclosporin A (CsA, manufactured by Wako Pure Chemical Industries, Ltd.) was administered to all the SD rats at a daily dose of 10 mg/kg. Four weeks after the transplantation of the donor cells, the brains of the SD rats were washed and fixed by intracardially perfusing 4% paraformaldehyde under deep anesthesia. On the day of necropsy, a blood sample was collected from each SD rat one hour after the final injection of the test compound or CsA. Such a sample was sent to SRL, Inc. (Tokyo, Japan) where the blood concentration of the administered drug (test compound) was measured.

Transplantation Experiment of Human iPS Cell-Derived Dopamine Neural Progenitor Cells Twelve-week-old SCID rats (produced by Institute of Laboratory Animals, Graduate School of Medicine, Kyoto University) were handled in accordance with the Guidelines for Animal Experiments of Kyoto University. The SCID rats were anesthetized, and donor cells were transplanted by stereotaxic injection into striatums on both sides. Dopamine neural progenitor cells ($2.7 \times 10^5$ cells on average) prepared from 1039A1 cell, that is, a human iPS cell line, were collected in 2 µl of PBS(-) so as to be used as the donor cells for the transplantation in each tract. To the PBS(-), Y-28632 was added at a final concentration of 30 µM. Thereafter, intraperitoneal injection of VPA (150 mg/kg/day or 600 mg/kg/day, which are sometimes designated respectively as a high dose and a low dose), ZNS sodium salt (30 mg/kg/day or 60 mg/kg/day, which are sometimes designated respectively as a high dose and a low dose), or a saline was conducted from two days before transplanting the donor cells until a day of necropsy. Four weeks after the transplantation of the donor cells, the brains of the SCID rats were washed and fixed by intracardially perfusing 4% paraformaldehyde under deep anesthesia. On the day of necropsy, a blood sample was collected from each SCID rat one hour after the final injection of the test compound, and the blood concentration of the drug (test compound) was measured.

Reverse Transcriptase Polymerase Chain Reaction (RT-PCR)

Total RNA was extracted by using RNeasy Plus Mini Kit (manufactured by Qiagen). The extracted total RNA was reverse transcribed by using Super Script III First-Strand Synthesis System (manufactured by Invitrogen). Each PCR was performed by using Hot StartTaq DNA polymerase (manufactured by Qiagen). A reverse transcriptase was not added so as to perform a control amplification reaction for each primer. MEF was used as another negative control. Gene sequences to be detected by the RT-PCR were all known, and on the basis of the gene sequences, the primers were designed and the molecular weights of amplified products were estimated.

Immunofluorescence

In an in vitro experiment, a cell aggregate treated with any of the above-described test compounds on day 14 after starting the SFEB was fixed with 4% paraformaldehyde. Thereafter, the fixed cell aggregate was frozen and sliced into thin sections each having a thickness of 10 µM by using a microtome for immunocytochemistry. On the other hand, in an in vivo experiment (transplantation experiment), the brain of a SD rat or a SCID rat was taken out after the transplantation experiment to be fixed again with 4% paraformaldehyde for 2 days. Thereafter, the fixed brain of the SD rat or SCID rat was cryopreserved in 30% sucrose for 3 days, frozen, and sliced into thin sections each having a thickness of 40 µM for immunohistochemistry. The frozen sections of the sphere (spherical cell mass) and the brain were subjected to a permeabilization and blocking treatment in PBS(-) for 1 hour at room temperature to be used as samples. The PBS(-) contained 0.3% Triton-X and 2% donkey serum. Thereafter, each of the sections was incubated overnight together with a primary antibody at 4° C. Primary antibodies used in this example are a rabbit anti-tyrosine hydroxylase antibody (dilution rate of 1:400, TH; manufactured by Millipore), a mouse anti-TH antibody (dilution rate of 1:200, manufactured by Millipore), a sheep anti-TH antibody (dilution rate of 1:400, manufactured by Millipore), a mouse anti-Tubβ3 antibody (dilution rate of 1:1000, Tuj1; manufactured by Covance Inc.), a rat anti-NURR1 antibody (dilution rate of 1:1000, KAN Research Institute, Inc., Kobe, Japan), a rabbit anti-Ki67 antibody (dilution rate of 1:1000, manufactured by Novocastra: NCL-Ki67p), a rabbit anti-caspase 3 antibody (dilution rate of 1:500, manufactured by Santa Cruz Biotechnology, Inc.), a rat anti-M2M6 antibody (dilution rate of 1:50, manufactured by Developmental Study Hybridoma Bank), a mouse anti-Nestin antibody (dilution rate of 1:50; manufactured by Millipore), a rabbit anti-Pitx3 antibody (dilution rate of 1:500; manufactured by Chemicon International Inc.), a goat anti-HNF-3β antibody (dilution rate of 1:500, Foxa2; manufactured by Santa Cruz Biotechnology, Inc.), a mouse anti-human Nuclei antibody (dilution rate of 1:1000; manufactured by Millipore), and a mouse anti-NeuN antibody (dilution rate of 1:500, manufactured by Chemicon International Inc.). After washing with PBS (0.05% Tween-20) three times, the resultant sample was incubated with an Alexa Fluor-conjugated secondary antibody for 1 hour at room temperature. After washing three more times, the sample was incubated with DAPI for nuclear staining and mounted using Permaflow (Dako). Immunoreactive cells were visualized with a confocal laser microscope (Fluoview FV1000D; manufactured by Olympus Corporation). In order to determine the percentage of positive cells for each marker, the number of labelled cells was manually counted in at least three independent experiments. The volume and the number of Ki67$^+$/Nestin$^+$ cells in each graft were determined by using BZ-II analysis software program (Keyence). In order to estimate the number of immunoreactive cells in each graft, the number of cells in every six grafts was manually counted, with Abercrombie Correction (Abercrombie, 1946) applied.

Statistical Analysis

Statistical analysis was carried out by using GraphPad Prism software program Ver. 5.0b (GraphPad Software). All quantitative data was indicated in the form of mean±SD (standard deviation), and One-way ANOVA and Newman-Keuls post-hoc tests were used. Differences were considered to be statistically significant for $P<0.05$.

Results

Figure 2:
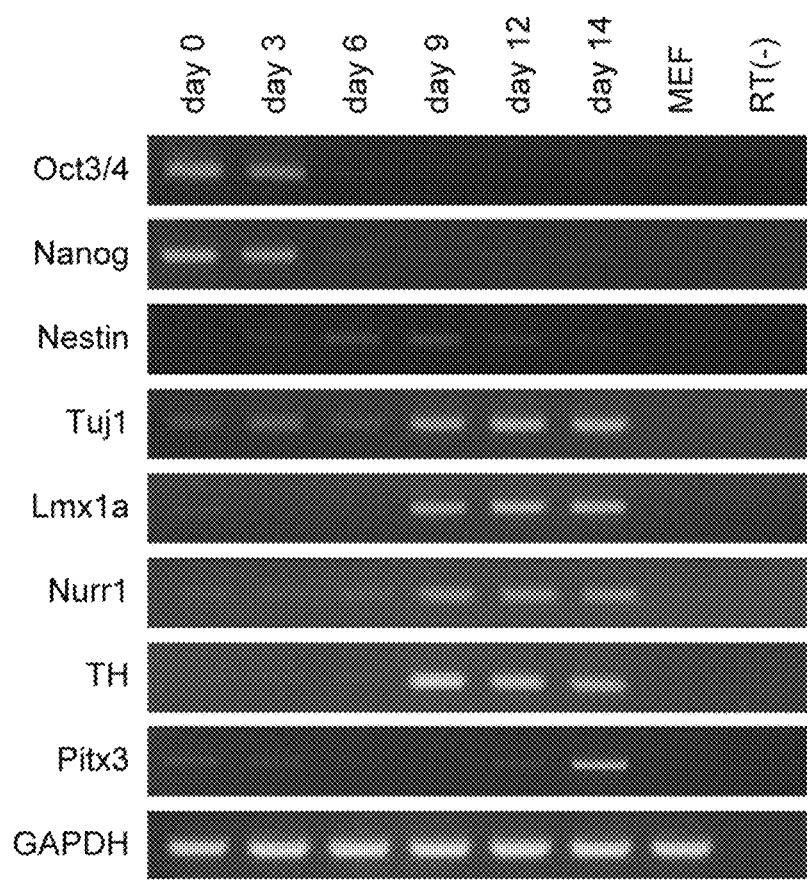
FIG. 2 illustrates RT-PCR results showing expression time-course of respective marker genes caused by the differentiation of mouse iPS cells through neural progenitor cells into midbrain dopaminergic neurons.

Differentiation of Dopaminergic Neurons from Mouse iPS Cells Dopaminergic neurons were differentiation induced from 440A3 cells, that is, a mouse iPS cell line, by employing the SFEB. The 440A3 cells proliferated continuously until day 14 after starting the SFEB. In accordance with the differentiation induction, expression of Nanog-GFP was gradually reduced, and the expression was not substantially observed on day 9 after starting the SFEB. RT-PCR photographs showing change with time of the expression of respective gene markers are illustrated in FIG. 2. It was confirmed that cell aggregates having pluripotency (Oct3/4$^+$, Nanog$^+$) were differentiated into immature neural progenitor cells (NPC) (Nestin$^+$) on day 6 to 9 after starting the SFEB, and thereafter differentiated into Tuj1$^+$ neurons (FIG. 2). The Tuj1$^+$ neurons also expressed Lmx1a, Nurr1 and TH, that are, dopaminergic neuron-specific markers.

The obtained cells also contained undifferentiated cells and non-neural cells. Therefore, in order to obtain a highly homogeneous population of NPC, PSA-NCAM$^+$ cells were sorted by using the FACS. PSA-NCAM is a cell adhesion molecule specifically expressed on the surface of a neural cell. On day 9 after starting the SFEB, about 60% of the cells were positive for PSA-NCAM (PSA-NCAM$^+$). The PSA-NCAM$^+$ cells sorted by the FACS were made to re-aggregate and allowed to mature for another 5 days. The matured cells were subjected to immunocytochemistry. When a section of the matured cell aggregate was immunofluorescence stained, most of cells were Tuj1$^+$ neurons, in which midbrain dopaminergic neurons were present.

The dopaminergic neurons simultaneously expressed TH, NURR1, FOXA2 and PITX3.

Influence of VPA and E2 on Differentiation into Dopaminergic Neurons in vitro

Figure 3:
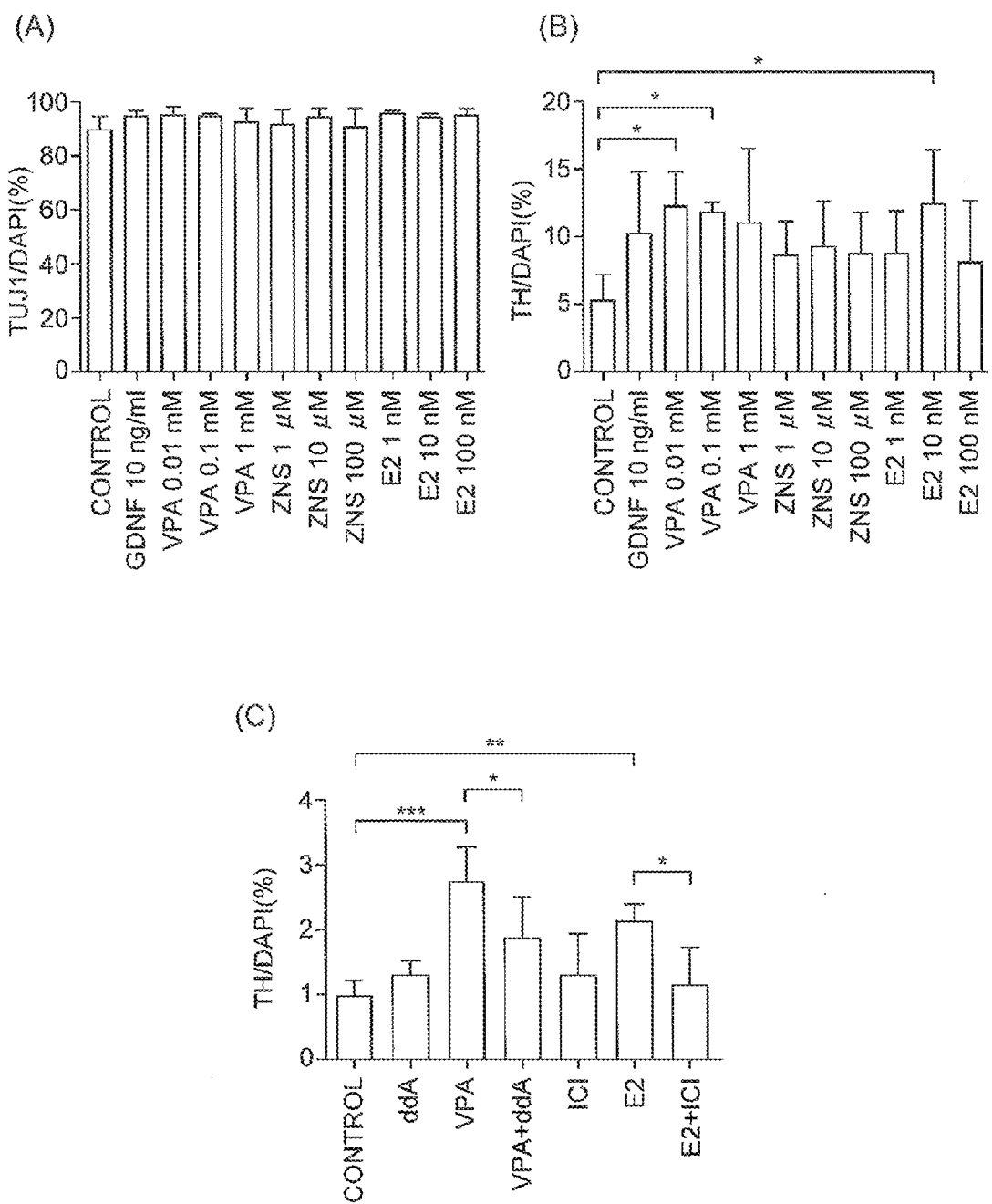
FIG. 3 illustrates graphs, obtained in in vitro experiments, of expression levels of respective marker molecules of neural progenitor cells derived from mouse iPS cells.

It was examined whether or not VPA, ZNS and E2 affect the differentiation induction into dopaminergic neurons in vitro. From day 10 to day 14 after starting the SFEB, re-aggregated PSA-NCAM$^+$ cells were cultured in the presence of VPA, ZNS or E2. When the immunocytochemistry was performed on day 14 after starting the SFEB, 90% or more of cells expressed Tuj1, that is, a neuronal marker, in using any of the test compounds (FIG. 3(A)). In control cells, 5.2±1.1% of cells were TH$^+$. On the contrary, in cells cultured respectively in the presence of VPA (0.01 mM and 0.1 mM) and E2 (10 nM), ratios of TH$^+$ cells were increased about twice as large as that of the control (which ratios were 12.1±1.5%, 11.7±0.4% and 12.2±2.3%, respectively) (FIG. 3(B)). In order to investigate whether or not such an effect of VPA and E2 was caused via the cyclic AMP pathway or the estrogen receptor, ddA, that is, an adenylate cyclase inhibitor, and ICI, that is, an estrogen receptor antagonist, were respectively used. When cells were cultured with 100 μM of ddA and 2 μM of ICI respectively added to 0.1 mM of VPA and 10 nM of E2, the ratios of increase in the TH$^+$ cells were remarkably reduced (FIG. 3(C)). On the other hand, even if ddA or ICI was singly added to cells, the ratio of TH$^+$ cells was not changed as compared with that of the control.

Figure 4:
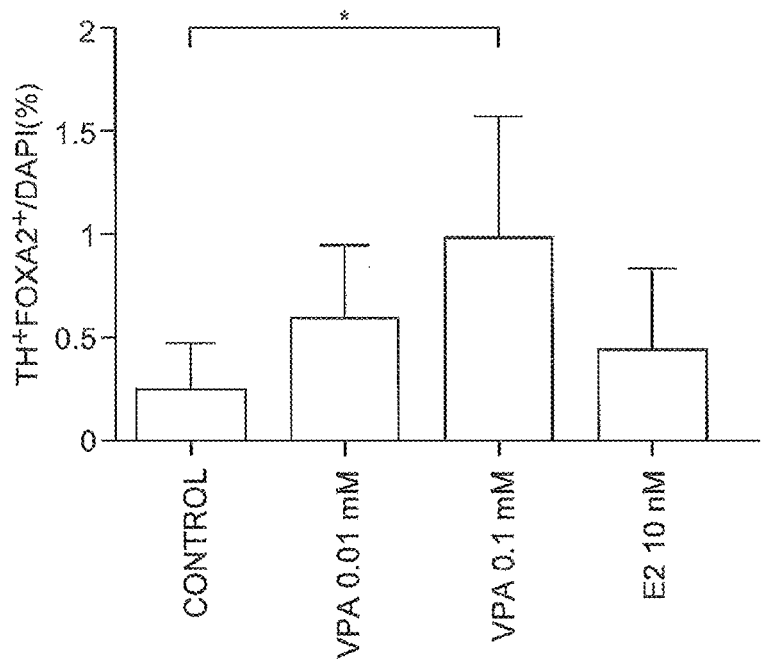
FIG. 4 illustrates graphs, obtained in in vitro experiments, of expression levels of respective marker molecules of midbrain dopaminergic neurons derived from mouse iPS cells.
Figure 4:
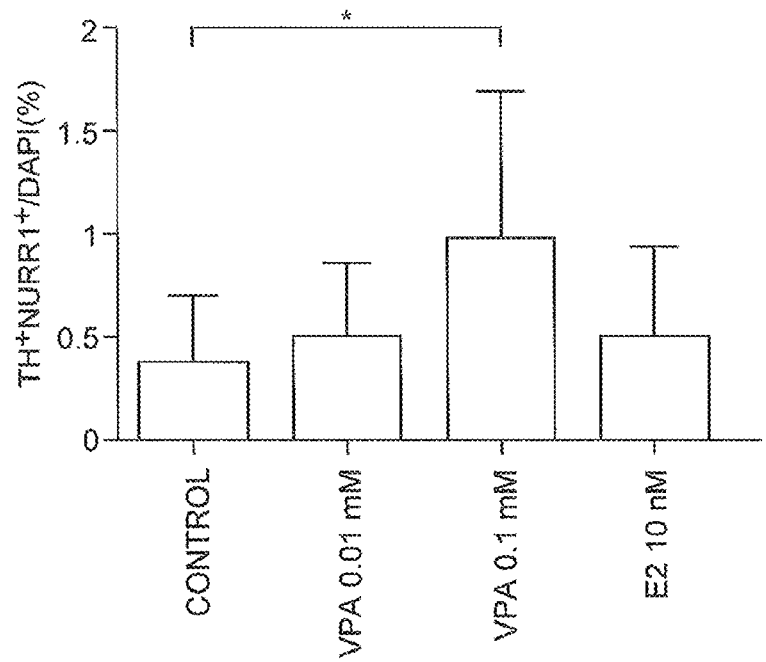

Next, double-label immunocytochemistry was conducted for marker molecules of midbrain dopaminergic neurons such as FOXA2, NURR1, PITX3 and TH. In cells cultured with 0.1 mM of VPA added, ratios of TH$^+$ FOXA2$^+$ cells and TH$^+$ NURR1$^+$ cells were remarkably increased as compared with those of controls (which ratios were respectively 1.00±0.58% vs. 0.25±0.22% and 1.00±0.70% vs. 0.37±0.32%, FIG. 4). Since a time period of the differentiation induction was too short and the cells were cultured without adding a cytokine such as GDNF, PITX3$^+$ cells were substantially not observed. These results suggested that the differentiation into dopaminergic neurons and the acquisition of midbrain-like dopaminergic neuron phenotype are accelerated by culturing cells with VPA.

Next, with expression of caspase 3, that is, a marker of apoptosis cells, used as an index, the influence of the above-described test compounds on the survival rate of TH$^+$ neurons in vitro was evaluated. In a control sphere, 18.0±5.9% of TH$^+$ neurons expressed caspase 3.

Figure 5:
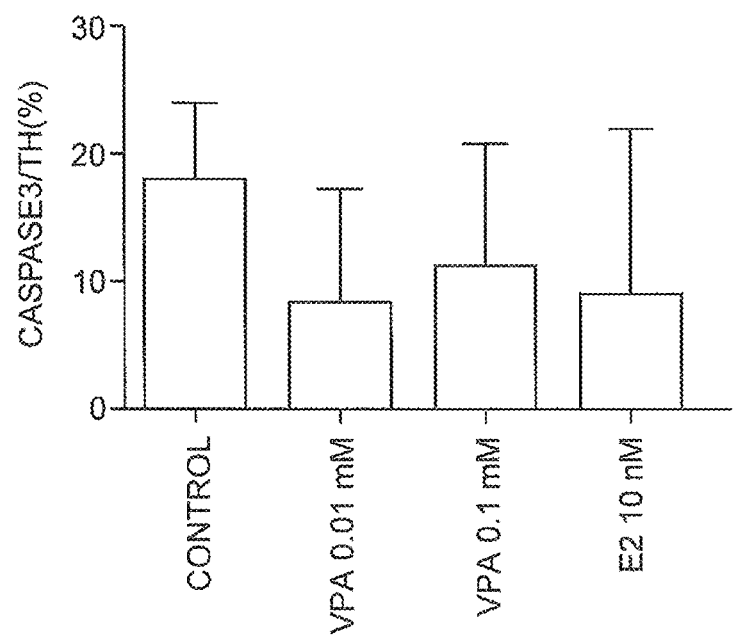
FIG. 5 illustrates a graph, obtained in in vitro experiments, of an expression level of caspase 3 of midbrain dopaminergic neurons derived from mouse iPS cells.

This result suggested that one-fifth of dopaminergic neurons were undergoing apoptosis (FIG. 5). On the other hand, in cells cultured in the presence of VPA or E2, a ratio of dopaminergic neurons undergoing apoptosis was low. Among four groups, however, there was no significant difference.

Influence of VPA on Differentiation of Transplanted NPC into Neurons

Next, it was examined whether or not the systemic administration of VPA, ZNS or E2 affects the survival rate and differentiation of dopaminergic neurons in a graft. In this transplantation experiment, on day 9 after starting the SFEB, a cell population ($3.1 \times 10^5$ cells in two aggregates, in PBS) not sorted by the FACS was transplanted into a striatum of a SD rat. To the SD rat used for the transplantation, one of the above-described agents and CsA, that is, an immunosuppressive agent, were intraperitoneally administered every day from two days before the transplantation until a day of sacrifice (for four weeks after the transplantation). On the day of sacrifice, the blood concentration of CsA was 3700±898 ng/ml on average. The blood concentrations of VPA, ZNS and E2 were respectively 158.5±3.9 μg/ml, 2.43±0.13 μg/ml and 1141±926 pg/ml.

Figure 6:
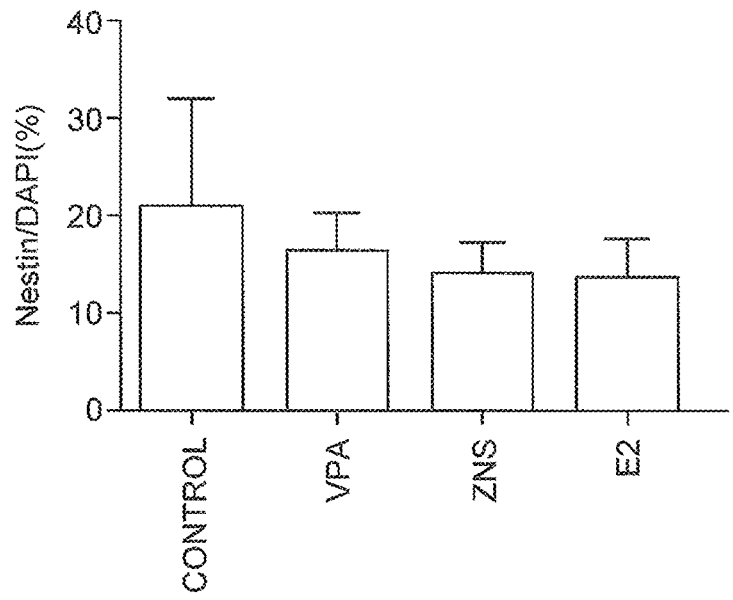
FIG. 6 illustrates graphs, obtained in in vivo experiments, of expression levels of respective marker molecules in grafts derived from mouse iPS cells.
Figure 6:
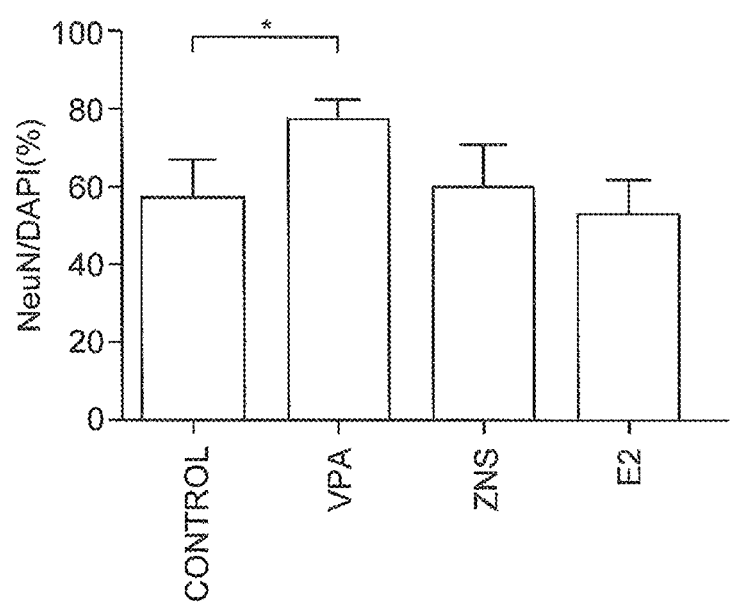
Figure 7:
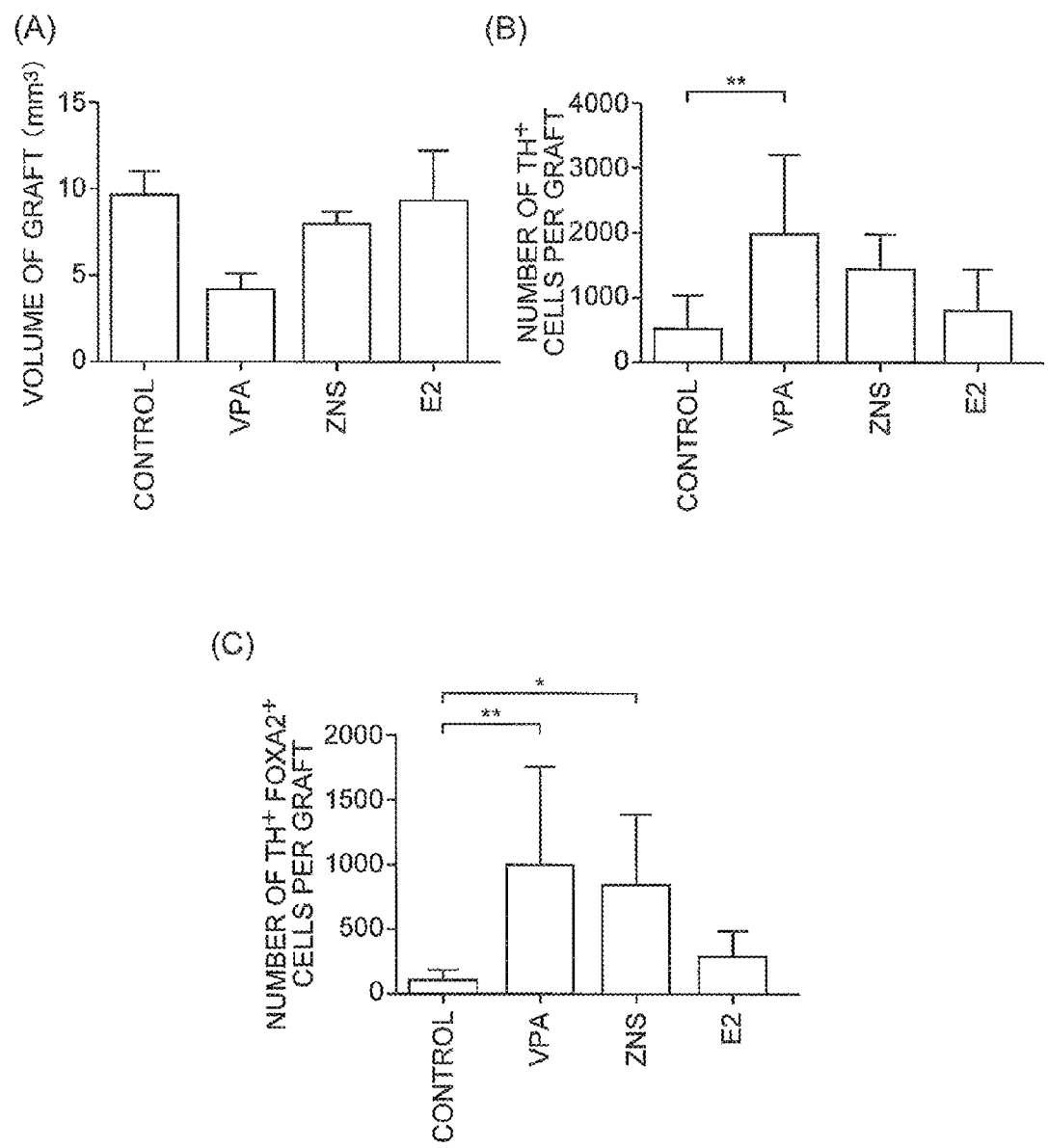
FIG. 7 illustrates graphs, obtained in in vivo experiments, of the volumes of grafts derived from mouse iPS cells and the numbers of midbrain dopaminergic neurons present in the grafts.

When the double-label immunohistochemistry was performed for Nestin (a marker of NPC) and Ki67 (a marker of proliferating cells), 15 to 20% of transplanted cells were Nestin$^+$ cells, but there was no significant difference among four groups (FIG. 6(A)). A ratio of Ki67$^+$ cells in Nestin$^+$ cells was very low ($<0.1\%$) in all grafts. It was suggested that the Nestin$^+$ cells were mostly quiescent or becoming post-mitotic at this time point. On the other hand, when the immunohistochemistry was performed for NeuN, that is, a marker of mature neurons, in a SD rat administered with VPA, a ratio of NeuN$^+$ cells to the number of all the cells in a graft was significantly increased as compared with that in a control SD rat (which ratio was 77.9±5.1% vs. 57.7±9.4%, FIG. 6(B)). This result suggested that VPA accelerates the differentiation of transplanted NPC into neurons. The grafted cells were identified using immunofluorescent staining for M2M6. The M2M6 is expressed merely in grafted cells (mouse cells) and is not expressed in cells of the SD rat, that is, a host. Four weeks after the transplantation, grafts satisfactorily survived and no signs of tumor formation were observed in all the groups. Regarding the volume of graft, that of the SD rat administered with VPA was smallest (4.33±2.14 mm$^3$), and that of the control SD rat was largest (9.76±3.19 mm$^3$) There was, however, no significant difference (FIG. 7(A)).

Improvement, attained by Administration of VPA or ZNS, of Retention Rate of Midbrain Dopaminergic Neurons in Graft containing Mouse iPS Cell-derived Neural Progenitor Cells The number of TH$^+$ cells in a graft obtained four weeks after the transplantation was compared among four groups. When the double-label immunohistochemistry was performed, the number of TH$^+$ cells in a graft of a SD rat administered with VPA was remarkably large as compared with that in a graft of a control SD rat (wherein numbers were respectively 1396±864 cells and 393±311 cells, FIG. 7(B)). In the graft of the control SD rat, merely a part of the TH$^+$ cells co-expressed FOXA2, that is, a midbrain marker (24.7±9.3%). On the contrary, in grafts of SD rats respectively administered with VPA and ZNS, most of the TH$^+$ cells were FOXA2$^+$ (the ratios of which were respectively 81.8±33.6% and 80.4±21.1%). It was revealed, through statistical analysis, that the number of midbrain dopaminergic neurons (TH$^+$ FOXA2$^+$) in a graft of a SD rat administered with VPA or ZNS was significantly increased as compared with that in a graft of a control SD rat (the numbers of which were respectively 984±770 cells, 835±540 cells and 97±76 cells, FIG. 7(C)). These results suggested that the retention rate of dopaminergic neurons differentiated from transplanted neural progenitor cells is improved by systemic administration of VPA or ZNS. When ZNS was administered, a ratio of the differentiation of the transplanted NPC into neurons was almost equivalent to that of a control (FIG. 6(B)), and hence, it was suggested that there is a mutually independent relationship between a retention rate attained after transplantation and efficiency of differentiation of NPC into neurons.

Figure 8:
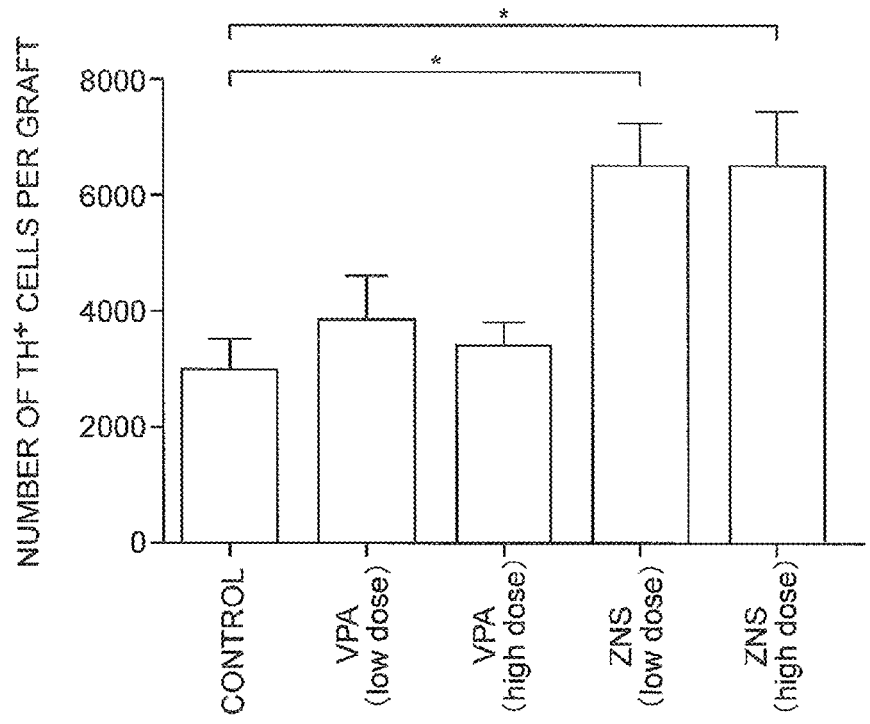
FIG. 8 illustrates graphs, obtained in in vivo experiments, of the numbers of midbrain dopaminergic neurons present in grafts derived from human iPS cells.
Figure 8:
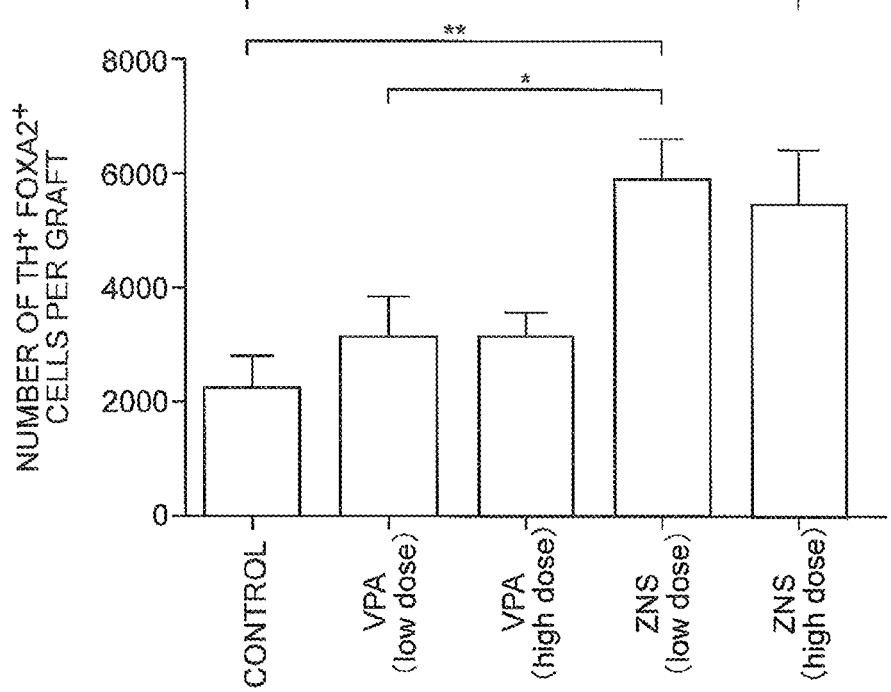

Survival Rate, attained by Administration of VPA or ZNS, of Midbrain Dopaminergic Neurons in Graft containing Human iPS Cell-derived Neural Progenitor Cells The number of TH$^+$ cells in a graft obtained four weeks after transplantation was compared among five groups. When the double-label immunohistochemistry was performed, the number of TH$^+$ cells in a graft of a SCID rat administered with ZNS at a high dose was remarkably large as compared with that in a graft of a control SCID rat (the numbers of which were respectively 6480±2145 cells and 3026±1349 cells, FIG. 8(A). A symbol "*" used in the drawing indicates p<0.05). While a ratio of cells co-expressing FOXA2, that is, a midbrain marker, in the TH$^+$ cells was 76.3±9.7% in the graft of the control SCID rat, 91.8±6.2% of the TH$^+$ cells were FOXA2$^+$ in the graft of the SCID rat administered with ZNS at a high dose. It was revealed, through statistical analysis, that the number of midbrain dopaminergic neurons (TH$^+$ FOXA2$^+$) in a graft of a SCID rat administered with ZNS at a high dose is significantly increased as compared with that in a graft of a control SCID rat (the numbers of which were respectively 5889±1821 cells and 2297±1116 cells, FIG. 8(B). Symbols "*" and "**" used in the drawing respectively indicate p<0.05 and p<0.01.). These results suggested that the retention rate of dopaminergic neurons differentiated from transplanted neural progenitor cells is improved by the systemic administration of ZNS.

INDUSTRIAL APPLICABILITY

A transplantation adjuvant of the present invention is useful for improving, in transplantation of neural progenitor cells, particularly iPS cell-derived neural progenitor cells, a retention rate of dopaminergic neurons in a transplantation site of a recipient's brain. Besides, if the transplantation adjuvant contains valproic acid, the transplantation adjuvant is also useful for accelerating differentiation of the neural progenitor cells into dopaminergic neurons.

The invention claimed is:

1. A method of treating a degenerative disease of dopaminergic neurons in a subject in need thereof, comprising
    transplanting neural progenitor cells in the subject, and
    administering zonisamide to the subject before, after, or simultaneously with the transplanting,
    wherein the method excludes administering valproic acid.

2. The method according to claim 1, wherein the administering is performed no sooner than two days before the transplanting.

3. The method according to claim 1, wherein the neural progenitor cells are derived from iPS cells.

4. The method according to claim 1, wherein the degenerative disease of dopaminergic neurons is Parkinson's disease.

5. The method according to claim 1, wherein the administering is performed before the transplanting.

6. The method according to claim 1, wherein the administering is performed after the transplanting.

7. The method according to claim 2, wherein the administering is performed after the transplanting.

8. The method according to claim 1, wherein the subject is human.

9. The method according to claim 1, wherein the zonisamide is administered in an amount effective to increase a graft survival rate of dopaminergic neurons induced from the neural progenitor cells.

10. The method according to claim 1, wherein the zonisamide is administered in an effective amount from 10 to 600 mg per day of the zonisamide.

11. The method according to claim 1, wherein the zonisamide is administered in an amount that is more than 25 mg and 600 mg or less per day of the zonisamide.

12. A method of improving retention rate of dopaminergic nerve cells induced from neural progenitor cells after transplantation, comprising
    transplanting neural progenitor cells in a subject, and
    administering an effective amount of zonisamide to the subject before, after, or simultaneously with the transplanting wherein the method excludes administering valproic acid.

13. The method according to claim 12, wherein the administering is performed no sooner than two days before the transplanting.

14. The method according to claim 12, wherein the neural progenitor cells are derived from iPS cells.

15. A method of treating a degenerative disease of dopaminergic neurons, comprising the method of improving retention rate of dopaminergic nerve cells induced from neural progenitor cells after transplanting according to claim 12.

16. The method according to claim 15, wherein the degenerative disease of dopaminergic neurons is Parkinson's disease.

17. The method according to claim 12, wherein the administering is performed before the transplanting.

18. The method according to claim 12, wherein the administering is performed after the transplanting.

19. The method according to claim 12, wherein the subject is human.

* * * * *